(12) United States Patent
Ellman (10) Patent No.: US 10,842,554 B2
(45) Date of Patent: Nov. 24, 2020

(54) ELECTROSURGICAL ELECTRODE

(71) Applicant: Alan Ellman, Hewlett, NY (US)

(72) Inventor: Alan Ellman, Hewlett, NY (US)

(*) Notice: Subject to any disclaimer, the term of this patent is extended or adjusted under 35 U.S.C. 154(b) by 839 days.

(21) Appl. No.: 14/939,832

(22) Filed: Nov. 12, 2015

(65) Prior Publication Data

US 2016/0135880 A1    May 19, 2016

Related U.S. Application Data

(60) Provisional application No. 62/079,446, filed on Nov. 13, 2014.

(51) Int. Cl.
*A61B 18/14* (2006.01)
*A61B 18/00* (2006.01)
*A61B 18/12* (2006.01)
*A61B 18/04* (2006.01)

(52) U.S. Cl.
CPC .......... *A61B 18/148* (2013.01); *A61B 18/042* (2013.01); *A61B 2018/00077* (2013.01); *A61B 2018/00166* (2013.01); *A61B 2018/00196* (2013.01); *A61B 2018/00339* (2013.01); *A61B 2018/126* (2013.01); *A61B 2018/1253* (2013.01); *A61B 2018/1417* (2013.01); *A61B 2018/1467* (2013.01); *A61B 2018/1472* (2013.01); *A61B 2018/1475* (2013.01); *A61B 2018/1497* (2013.01); *A61B 2218/002* (2013.01); *A61B 2218/007* (2013.01)

(58) Field of Classification Search
CPC . A61B 18/148; A61B 18/042; A61B 18/1492; A61B 2018/1432; A61B 2018/1465; A61B 2018/1467
See application file for complete search history.

(56) References Cited

U.S. PATENT DOCUMENTS

| | | | | |
|---|---|---|---|---|
| 9,078,665 | B2* | 7/2015 | Moss | A61B 18/1487 |
| 2002/0049438 | A1* | 4/2002 | Sharkey | A61B 18/1402 |
| | | | | 606/41 |
| 2002/0128639 | A1* | 9/2002 | Pless | A61B 17/22012 |
| | | | | 606/27 |
| 2003/0130711 | A1* | 7/2003 | Pearson | A61B 18/1477 |
| | | | | 607/101 |
| 2005/0043728 | A1* | 2/2005 | Ciarrocca | A61B 18/1482 |
| | | | | 606/48 |
| 2012/0150165 | A1* | 6/2012 | Conley | A61B 18/1482 |
| | | | | 606/33 |
| 2012/0150172 | A1* | 6/2012 | Ortiz | A61B 18/1477 |
| | | | | 606/41 |
| 2013/0006232 | A1* | 1/2013 | Pellegrino | A61B 17/3472 |
| | | | | 606/33 |
| 2013/0310833 | A1* | 11/2013 | Brown | A61B 17/1114 |
| | | | | 606/45 |

* cited by examiner

Primary Examiner — Michael F Peffley
Assistant Examiner — Bo Ouyang (57) ABSTRACT

One embodiment of the present invention relates to an electrosurgical device for conducting surgery. The device includes a tubular housing and a plurality of electrodes disposed within said tubular housing. The device further includes an actuator connected to the plurality of electrodes to extend and retract at least one of the plurality electrodes to and from the tubular housing.

9 Claims, 11 Drawing Sheets

ELECTROSURGICAL ELECTRODE

CROSS REFERENCE TO RELATED APPLICATIONS

This application claims priority to provisional patent application 62/079,446, the entirety of which is hereby incorporated by reference.

BACKGROUND

The present invention relates to surgery performed on a patient by a surgical physician, a surgeon, and, more specifically, relates to back surgery. Specialized back surgery on or in-between vertebrae of the spine and on spinal discs involves various meticulous surgical procedures which can be challenging, even for experienced surgeons who specialize in this particular surgery. Minimally invasive techniques are preferred over traditional open surgical procedures which require extensive operating time and post-operative recovery time.

When employing minimally invasive surgical techniques on or between spinal vertebrae or on discs, one of the challenging requirements relates to providing electrodes of an electrosurgical device into the operative field.

SUMMARY OF THE INVENTION

One embodiment of the present invention relates to an electrosurgical device for conducting spinal surgery. The device includes a tubular housing and a plurality of electrodes disposed within said tubular housing. The device further includes an actuator connected to the plurality of electrodes to extend and retract at least one of the plurality electrodes to and from the tubular housing.

DETAILED DESCRIPTION OF PREFERRED EMBODIMENTS

Figure 1:
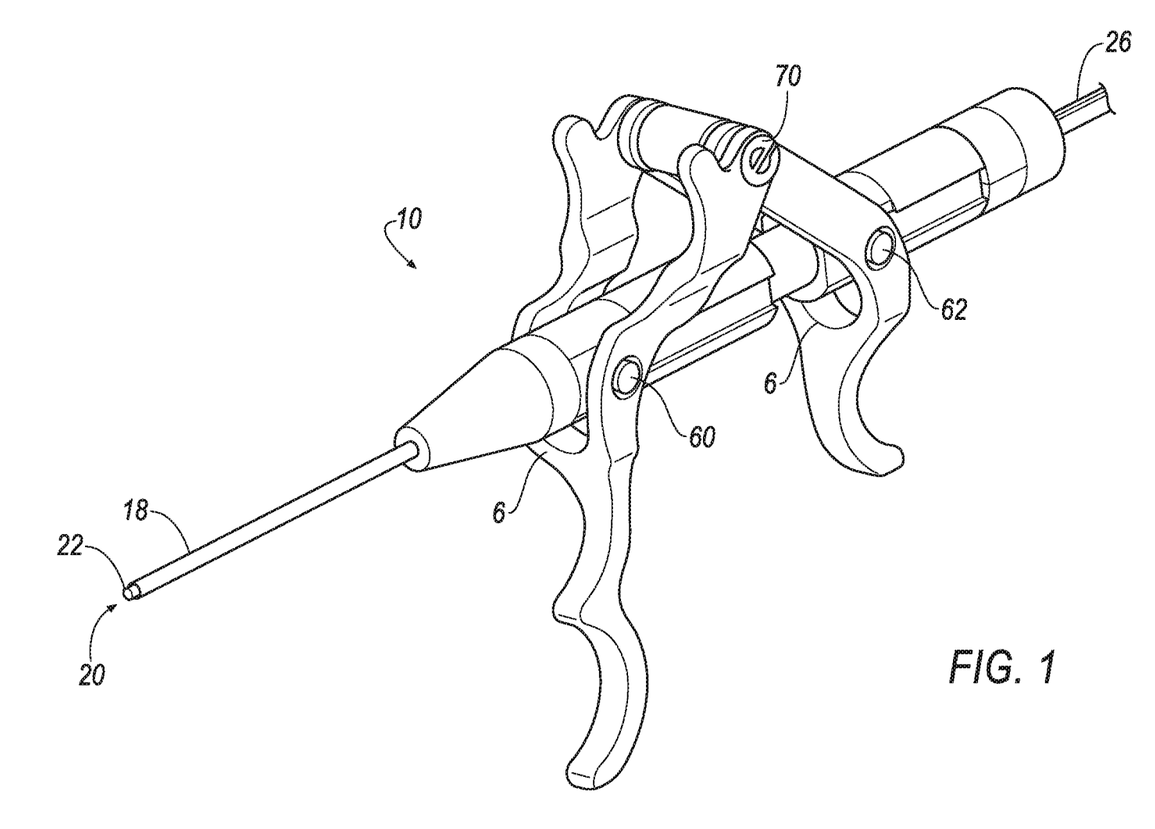
FIG. 1 is a perspective view of an electrosurgical instrument according to one aspect of the invention.
Figures 2, 3:
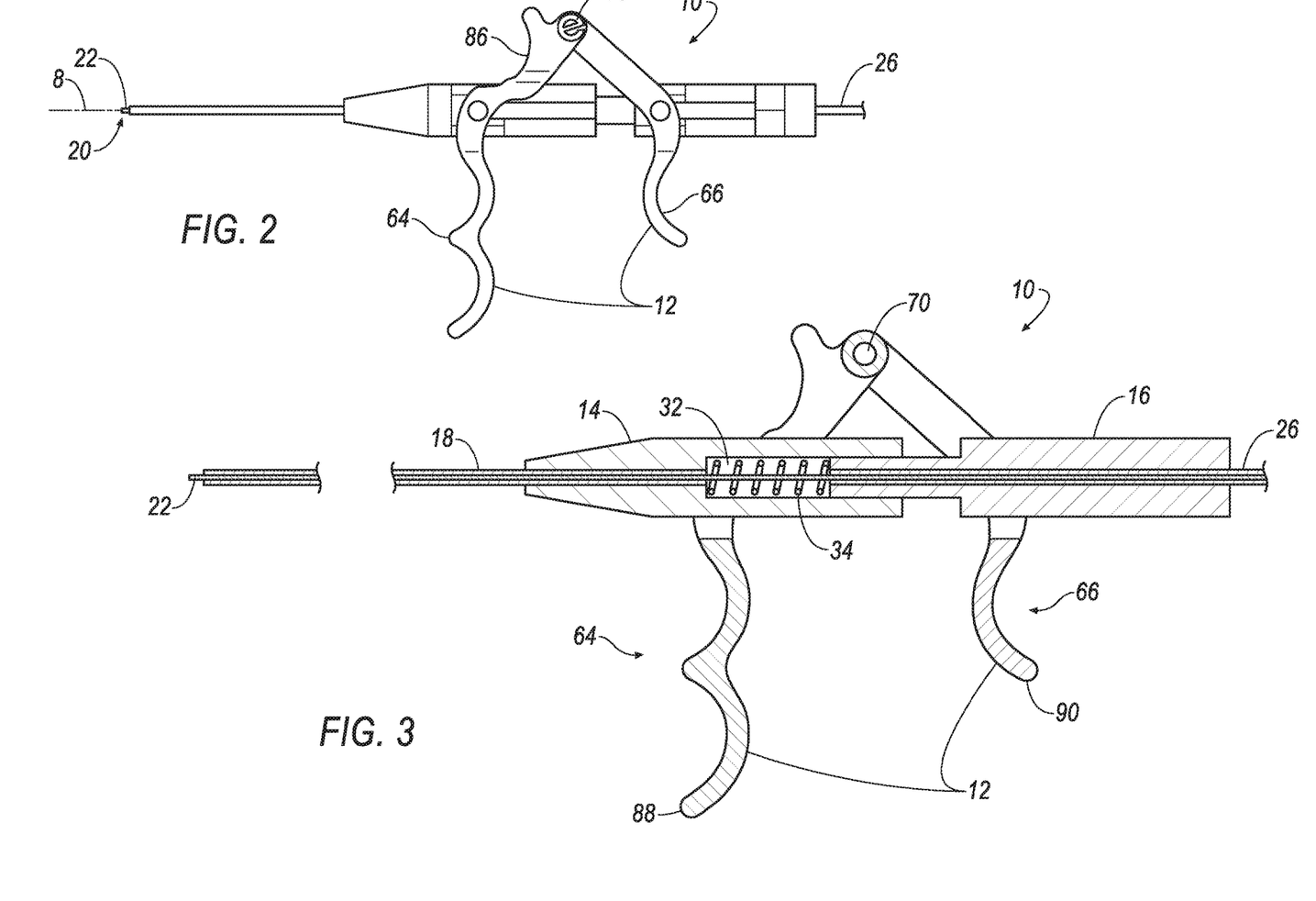
FIG. 2 is a plan view of an electrosurgical instrument according to one aspect of the invention.
FIG. 3 is a cross-sectional view of an electrosurgical instrument according to an aspect of the invention.
Figure 4:
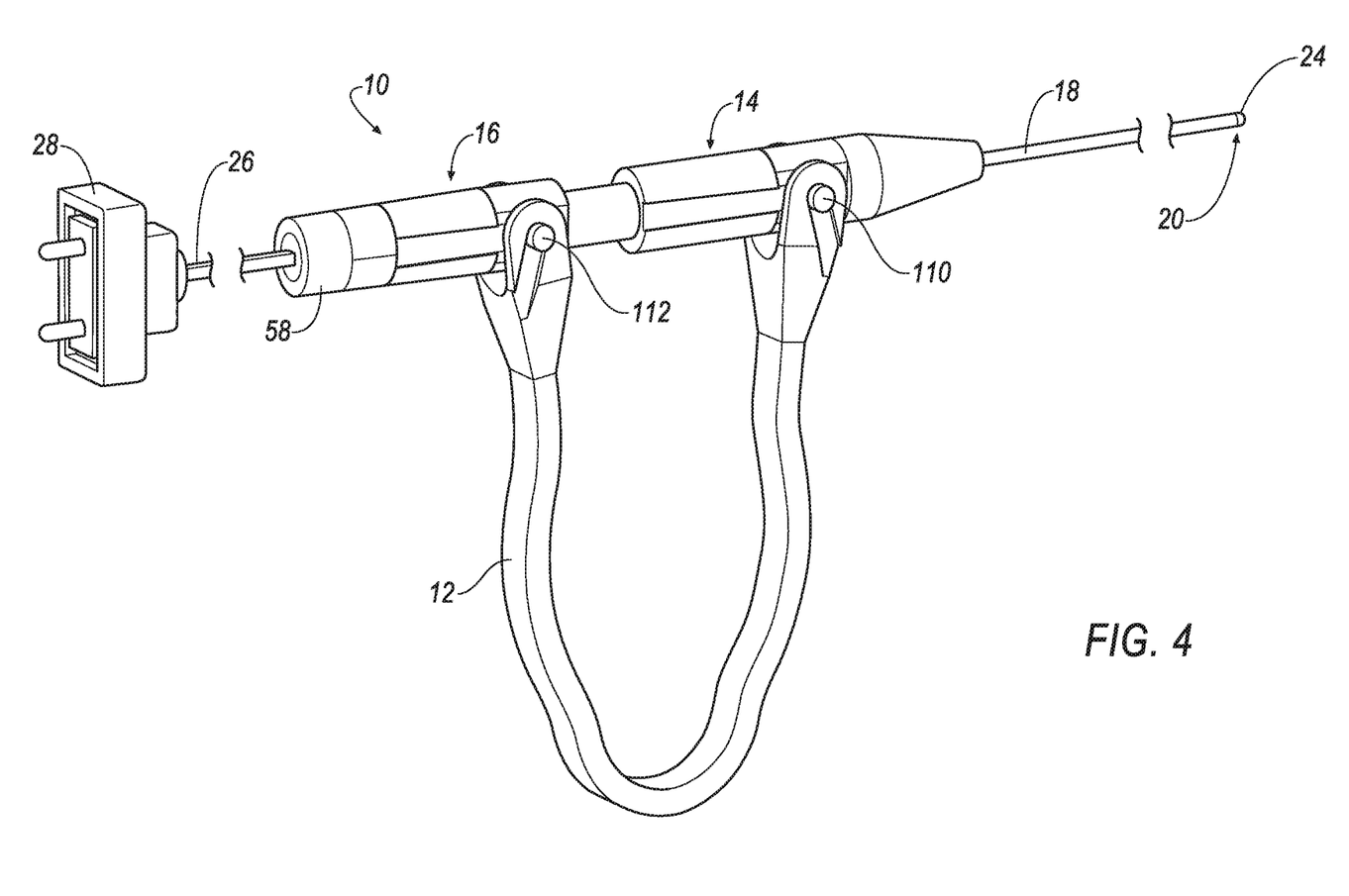
FIG. 4 is a perspective view of an electrosurgical instrument according to an aspect of the invention.

FIGS. 1 and 2 show one form of electrosurgical handpiece 10 according to one aspect of the invention, FIG. 3 shows a cross-sectional view, and FIG. 4 shows another form of electrosurgical handpiece 10. The present application incorporates U.S. Pat. Nos. 7,101,370; 7,222,644; 6,352,533 and 7,905,882 in their entirety by reference. It will be observed that the cross-sectional view of the handpiece interior of FIG. 3 is identical to that of FIG. 2 of the referenced patent. It comprises a squeezable handle 12 assembly connected to and across two front 14 and rear 16 main slideable coaxially-aligned body parts enclosing an elongated outer tubular housing 18 from whose distal end 20 an inner electrode assembly 22 can be extended and retracted when the handle 12 is squeezed or released, respectively. The handpiece common axis is designated 8 in FIG. 2. At the right end an electrical cord 26 is terminated in a plug connector (not shown). Internally of the handpiece, wires of the electrical cord 26 are connected to the active electrode assembly 22. The outer tubular housing 18 extends from the front at the left and through the center of the front body part 14. Although the tubular housing 18 is shown as tubular or cylindrical, it will be appreciated that other shapes such as diamond, oval, square or any other shape may be employed. The front body part 14 contains a bore 32 which houses a compression spring 34 engaged by a reduced diameter projecting member of the rear body part 16. The compression spring 34 biases apart the two body parts 14, 16. In one aspect, the handle 12 keeps the body parts 14, 16 from relatively axially rotating. However, the body parts may be keyed or other means to keep the two body parts from rotating. Each of the front and rear handle parts, designated generally 64 and 66, are rigid members from their lowest points, designated 88, 90, to where they join at the fulcrum axis 70. The electrode assembly, in one aspect, is affixed in rear body part 16 and slidable in tubular housing 18 such that squeezing of handle 12 causes electrode assembly 22 to extend from distal end 20.

Figure 5:
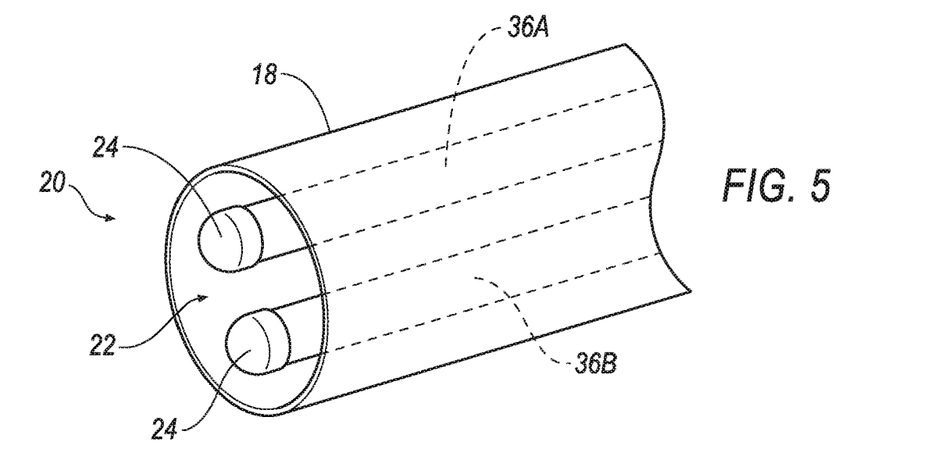
FIG. 5 is a perspective view of an electrosurgical electrode according to an aspect of the invention.

Referring now to FIG. 5, one embodiment of the distal end 20 of the electrosurgical handpiece 10 is shown and described. In FIG. 5, tubular housing 18 is shown encapsulating electrode assembly 22. Electrode assembly 22 includes first electrode 36A positioned adjacent and parallel to second electrode 36B. The electrodes are affixed in rear body part 16 such that actuation of the handle 12 causes the electrodes 24 to extend from the tubular housing 18. In one aspect, tubular housing 18 has a diameter of at least or approximately 6 mm. In the treatment of stenosis during spinal surgery, varying sizes of cannulas may be used and, in one aspect, a diameter of a cannula greater than 6 mm permits passage of tubular housing containing multiple electrode assemblies therethrough. However, one skilled in the art will recognize that the diameter of tubular housing 18 is not limited to that described herein and may be any diameter sufficient to support the electrodes.

In the embodiment shown in FIG. 5, first electrode 36A and second electrode 36B are shown not being separated by any material between each respective element or tubular housing 18. In such an arrangement, the space in-between the respective elements may be simply air and may assist in providing other features such as suction or the provision of fluids such as saline. Tubular housing 18 may be constructed of any number of material types including, but not limited to, metal, ceramics, plastics or other types of materials. In one aspect, tubular housing 18 is constructed of a dielectric or insulative material to prohibit electrical charge from being dissipated to tubular housing 18 or to a location outside tubular housing 18. One skilled in the art will recognize other variants to the aforementioned description. Each of the electrodes 36A or 36B include tip portions 24. Tip portions 24 will be described with respect to the following embodiments and descriptions.

Figure 6:
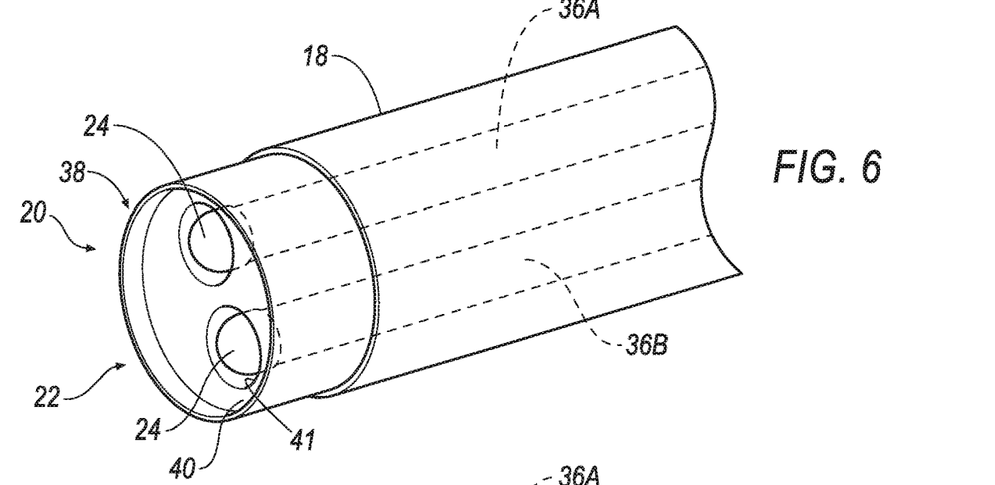
FIG. 6 is a perspective view of an electrosurgical electrode according to an aspect of the invention.

Referring now to FIG. 6, another embodiment of the present invention is shown and described. In FIG. 6, an insulating region 40 is provided and is positioned adjacent to and around each of the electrodes 36. Apertures 41 are recessed into the face region of the insulating region 42 to permit ingress and egress of each of the electrodes 36 as will be described in greater detail. Insulating region 42, in one aspect, insulates first electrode 36A from second electrode 36B. The apertures 41, in one aspect, assist in guiding the electrodes 36 when being moved from retracted to extended positions. Additionally, apertures 41 may be spaced apart at a desired distance to facilitate locating the electrodes 36 in a patient during a surgical procedure. In one example, the apertures 41 may be spaced relatively far apart such that the electrodes 36, when extended, are also positioned far part. Likewise, the electrodes 36 may be positioned relatively closer together such that, when extended, the electrodes are positioned relatively closer together. The insulating region 42 may be constructed of any dielectric or other insulating material and may extend from a planar surface of distal end of 22 to any desired depth. For example, insulating region 42 may extend the entire length of tubular housing 18 or it may extend only a certain predetermined distance from distal end 22 down tubular housing 18. Conductive sheath 38 is positioned inside tubular housing 18 and located between tubular housing 18 and insulating region 42. Conductive sheath 38 may be constructed of any conductive material including, but limited to, copper or silver. In one aspect, conductive sheath 38 is constructed of a non-oxidizing material such as gold to be used in connection with the surgical procedure.

Figure 7:
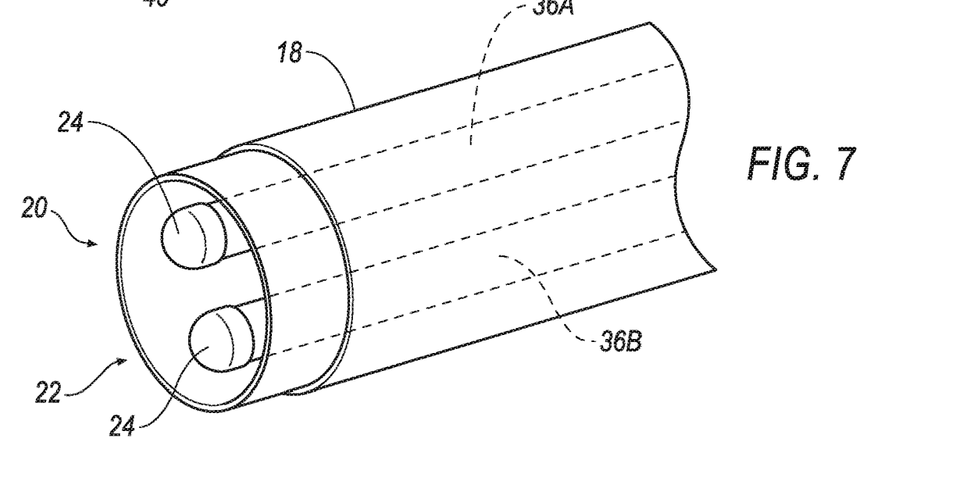
FIG. 7 is a perspective view of an electrosurgical electrode according to an aspect of the invention.

Referring now to FIG. 7, another embodiment of the present invention is shown and described. In FIG. 7, electrode assembly 22 is constructed similar to that of FIG. 6. However, in FIG. 7, insulating region 40 is removed leaving space between first electrode 36A, second electrode 36B, and conductive sheath 38. In this arrangement, suction may be provided through the spacing between the electrodes and the conductive sheath 38. Such suction may be provided by an external source, thereby drawing fluids and liquid from the operative field. In another aspect, various liquids or gases may be provided through the space such as plasma, saline, or argon into the operative field. In one aspect, the pressure of suction may be anywhere between 90-120 mm Hg. It will be understood that such section provision of liquids or gases in the present embodiment may be similarly applied to the embodiment shown in FIG. 5.

Figure 8:
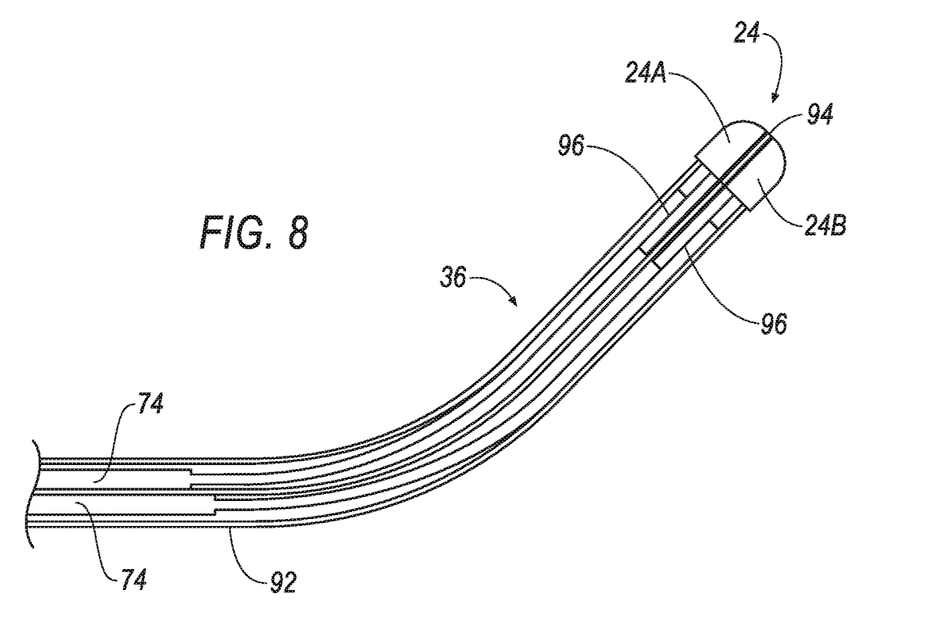
FIG. 8 is a cross-sectional view of an electrosurgical electrode according to an aspect of the invention.

With reference to FIG. 8, an embodiment of electrodes 36 is shown and described. Electrode 36 shown in FIG. 8 is a bipolar electrode. Wires 74 extend along the inside of sheath 92 in a parallel fashion separated by insulator 94. Sheath 92, in one aspect, insulates wires 74 from any external shorting or grounding to elements outside sheath 92. Wires 74 terminate at tip 24A and tip 24B through connection regions 96. Connection regions 96 may be soldered or welded connections or other suitable connections. Accordingly, electrical communication may be exhibited along each of the wires 74, through connection regions 96 and terminating at respective tip portion 24A or tip portion 24B. Tip portions 24A and 24B are conductive such that electrical signals provided by wires 74 are transmitted to the tip portions and respectively to the operative field or the patient.

Figure 9:
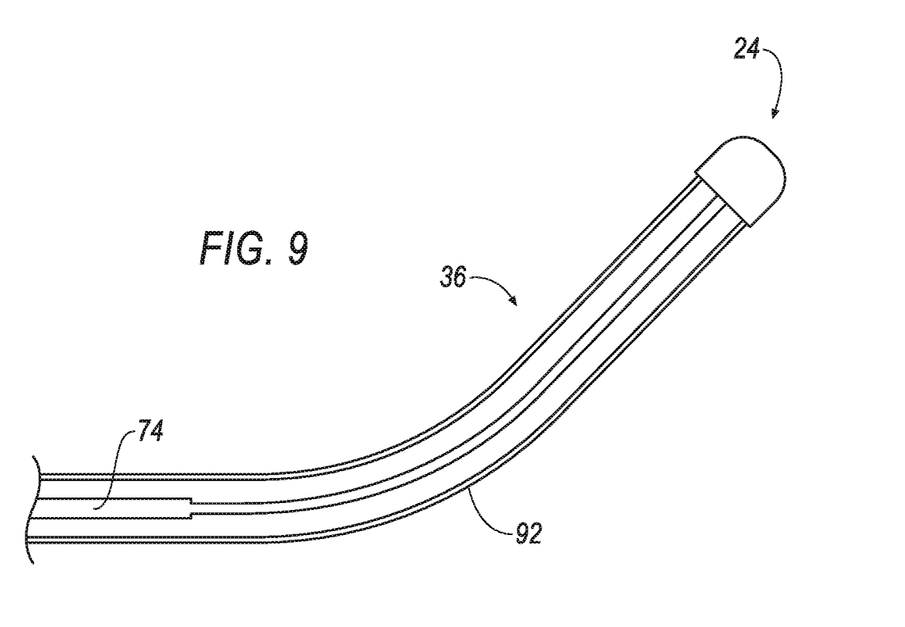
FIG. 9 is a cross-sectional view of an electrosurgical electrode according to an aspect of the invention.

Referring now to FIG. 9, another embodiment of the present invention is shown and described. In FIG. 9, electrode 36 includes a single wire 74 passing inside of sheath 92. As noted in the figure, electrode 36 does not include insulator 94 separating tip 24 into two separate sections. As such, electrical signals may be provided by wire 74 to tip 24. As will be understood, the present embodiment provides a monopolar electrode.

One skilled in the art will readily recognize that additional tip portions may be provided through adding additional wires 74, connection regions 96 and insulators 94. Accordingly, one skilled in the art will recognize that numerous additional portions may be provided including four, six, eight or any other number that may be supported by the sheath 92.

Figure 10:
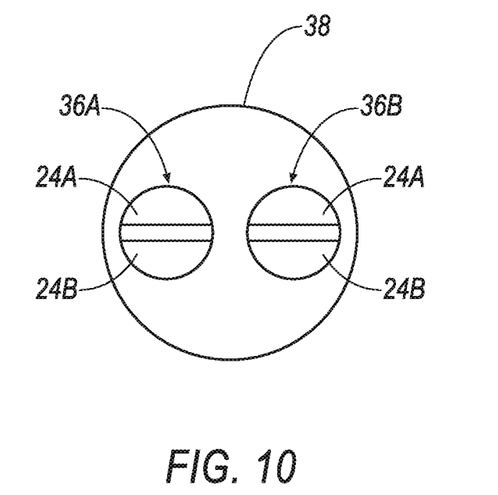
FIG. 10 is a plan view of a distal end of an electrosurgical electrode according to an aspect of the invention.

Referring now to FIGS. 10-13, various configurations of electrode assembly 22 are shown and described. The illustrations shown in FIGS. 10-13 are plan view schematics that correspond with FIGS. 5-7. In FIG. 10, conductive sheath 38 is shown encapsulating bipolar electrodes 24A and 24B. In the presently described embodiment, tip portions 24A and 24B of each of the electrodes 36A and 36B may have different polarities or neutral polarities. For example, for first electrode 36A, tip portion 24A may be positive while tip portion 24B is negative. Likewise, for electrode 36B, tip portion 24A may also be positive while tip portion 24B is negative. In such a configuration, the current direction for each positive tip portion will flow generally to the negatively charged tip portions or in accordance with convention. Conductive sheath 38 may also be negatively or positively charged, thereby influencing the current flow associated with the positively or negatively charged tip portions.

In another embodiment associated with FIG. 10, electrodes 36A and 36B may be monopolar electrodes that are positively charged while conductive sheath 38 is negatively charged. In such a situation, current flow would flow from each of the positively charged electrodes 36A and 36B to the negatively charged conductive sheath 38. Similarly, sheath 38 could be positively charged while each of the electrodes 36A and 36B are negatively charged. One skilled in the art will recognize various configurations through adjustment of the charges associated with each of the Lip portions 24 and the conductive sheath 38.

Figure 11:
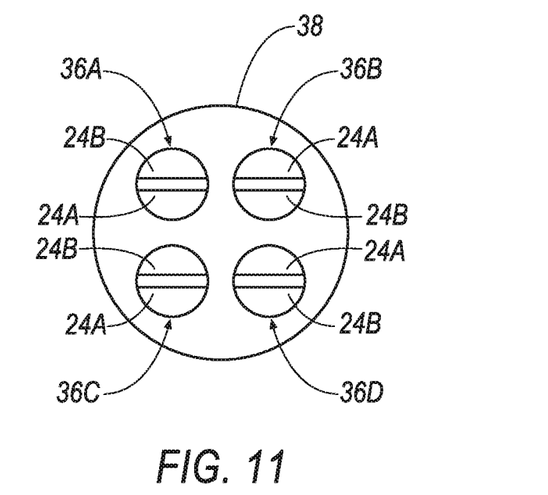
FIG. 11 is a plan view of a distal end of an electrosurgical electrode according to an aspect of the invention.

Referring now to FIG. 11, another embodiment of the present invention is shown and described. In FIG. 11, four separate bipolar electrodes are shown encapsulated by conductive sheath 38. Each of the tip portions 24A or 24B may be positively or negatively charged depending on the desired current flow characteristics desired. Likewise, conductive sheath 38 may also be positively or negatively charged. As such, current flow from any of the positively charged tip portions 24 to the respective opposite charged portion or conductive sheath 38 as the case may be.

Figure 12:
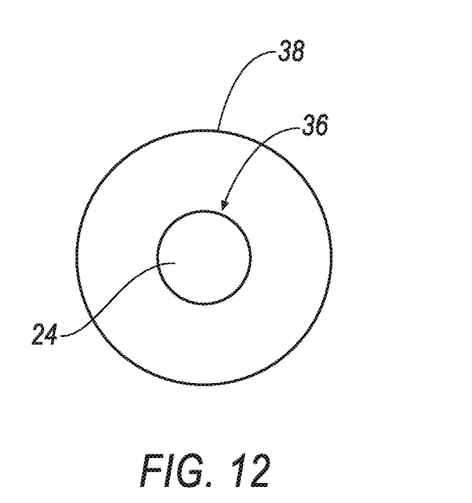
FIG. 12 is a plan view of a distal end of an electrosurgical electrode according to an aspect of the invention.

Referring now to FIG. 12, another embodiment of the present invention is shown and described. FIG. 12, a single monopolar electrode 36 is shown having a tip 24. Conductive sheath 38 encapsulates the monopolar electrode 36. In the present embodiment, monopolar electrode 36 is positively charged while conductive sheath 38 is negatively charged. Accordingly, current flows from electrodes 38, through the patient and to conductive sheath 38.

Figure 13:
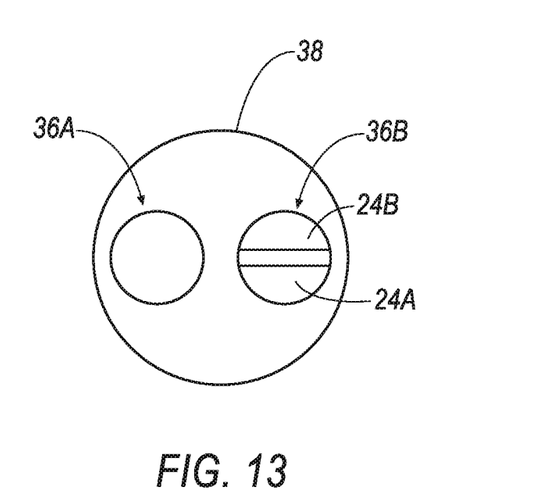
FIG. 13 is a plan view of a distal end of an electrosurgical electrode according to an aspect of the invention.

Referring now to FIG. 13, another embodiment of the present invention is shown and described. In FIG. 13, a monopolar electrode 36A is shown positioned adjacent to a bipolar electrode 36B. The monopolar electrode 36A and bipolar electrode 36B are encapsulated by conductive sheath 38. In the presently described configuration, the monopolar electrode may be positively charged while the bipolar electrode 36B has positively and negatively charged tip portions 24A and 24B respectively. In the present configuration, the surgeon may desire to utilize a monopolar electrode. In this instance, electrodes 30A is activated and extended with the positive charge while conductive sheath 38 provides a negative or ground charge. As such, current flows from electrodes 36A to conductive sheath 38. However, if the surgeon desires to utilize the bipolar electrode such as 36B, then the surgeon activates and extends electrode 36B by supplying positive charge to tip portion 24A and negative or ground to tip portion 24B to create a bipolar electrode. In this configuration, conductive sheath 38 is insulated such that it provides neither a ground or a positive charge.

Figure 14:
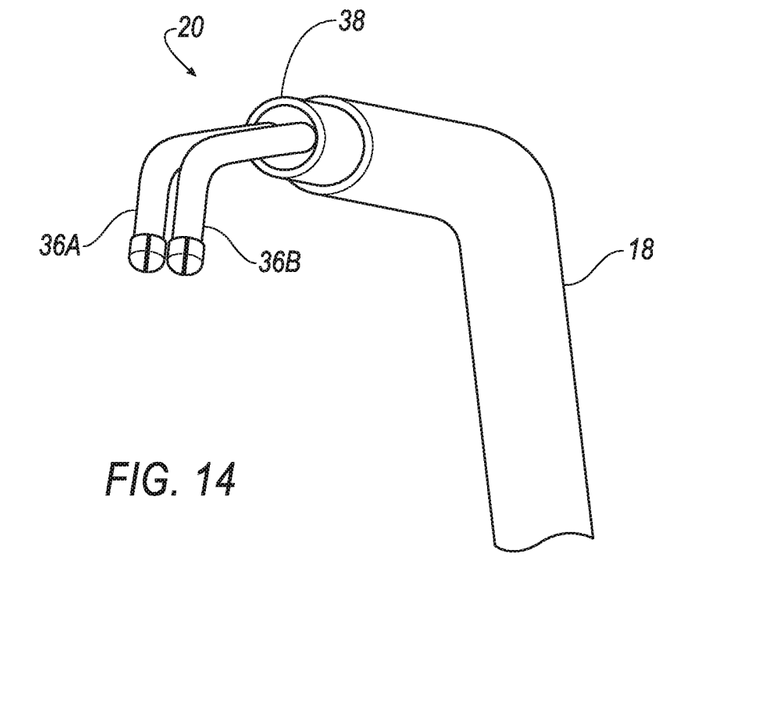
FIG. 14 is a perspective view of an electrosurgical electrode according to an aspect of the invention.

Referring now to FIG. 14, another aspect of the invention is shown and described. In FIG. 14, tubular housing 18 is shown having a curved portion. The curved portion curves each of the electrodes 36 such that the electrodes 36 exit the distal end 20 in a direction different from the axis of the remainder of the electrosurgical handpiece 10. In FIG. 14, electrodes are shown as electrode 36A and 36B. In one aspect, the embodiment shown in FIG. 14 corresponds with that shown in FIG. 10.

Figure 15:
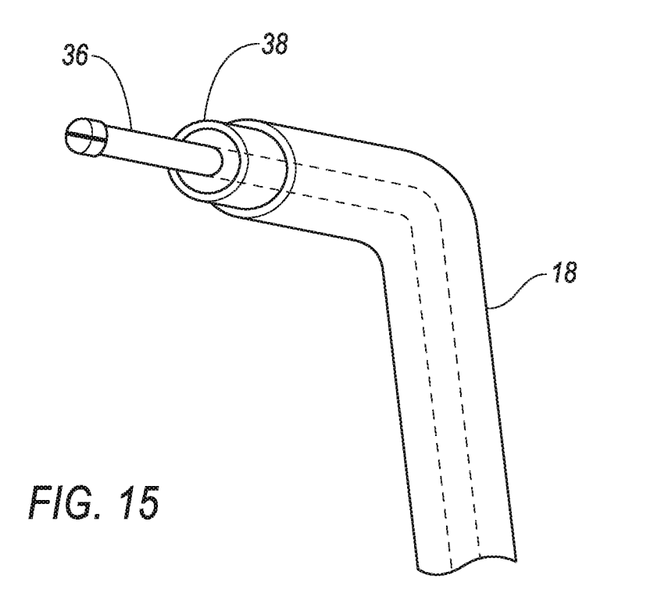
FIG. 15 is a perspective view of an electrosurgical electrode according to an aspect of the invention.
Figure 16:
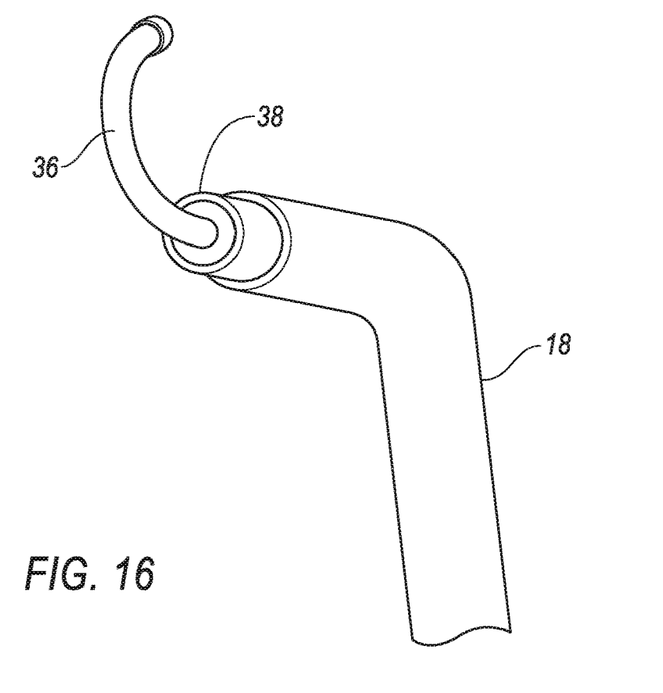
FIG. 16 is a perspective view of an electrosurgical electrode according to an aspect of the invention.
Figure 17:
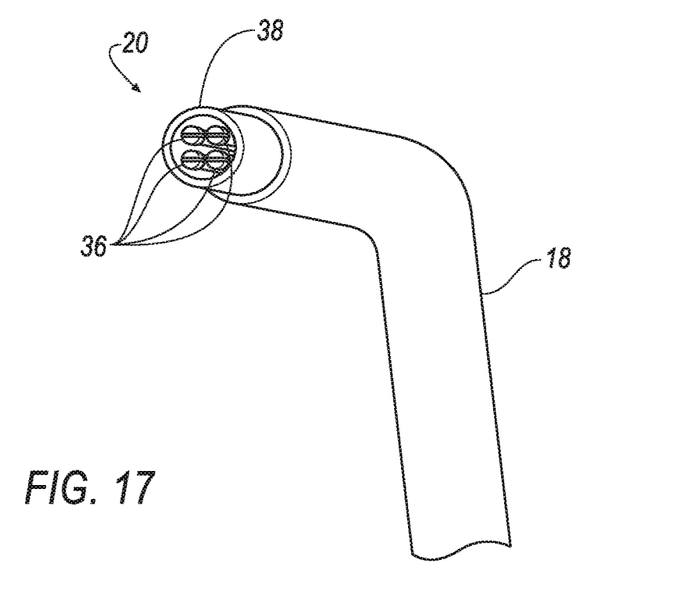
FIG. 17 is a perspective view of an electrosurgical electrode according to an aspect of the invention.
Figure 18:
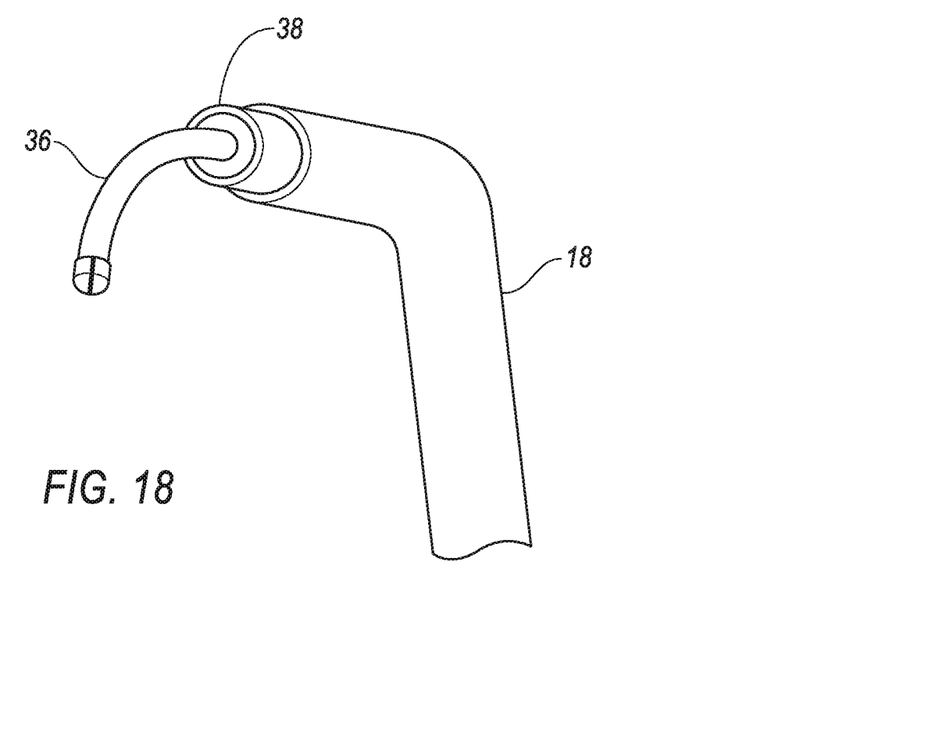
FIG. 18 is a perspective view of an electrosurgical electrode according to an aspect of the invention.

With reference to FIG. 15, another aspect of the invention is shown and described. FIG. 15 is similar as that described in FIG. 14. Electrode 36 in this embodiment is a single electrode that may be either a monopolar or bipolar electrode similar to that in FIG. 12. With reference to FIG. 16, another embodiment of the invention is shown and described. FIG. 16, a single electrode 36 which may be monopolar or bipolar shown curving in a direction toward parallel with the electrosurgical handpiece 10. Such curvature may be obtained through any number of methods including that depicted in any of the aforementioned patents incorporated by reference. With reference to FIG. 17, a perspective view is shown according to an aspect of the invention. The depiction in FIG. 17 corresponds to that of FIG. 11. With reference to FIG. 18, an embodiment of the invention is shown and described. In FIG. 18, electrode 36 is shown curved towards the electrosurgical handpiece 10. The curvature may be obtained through any means including that depicted in the aforementioned patents Incorporated by reference.

Figure 19:
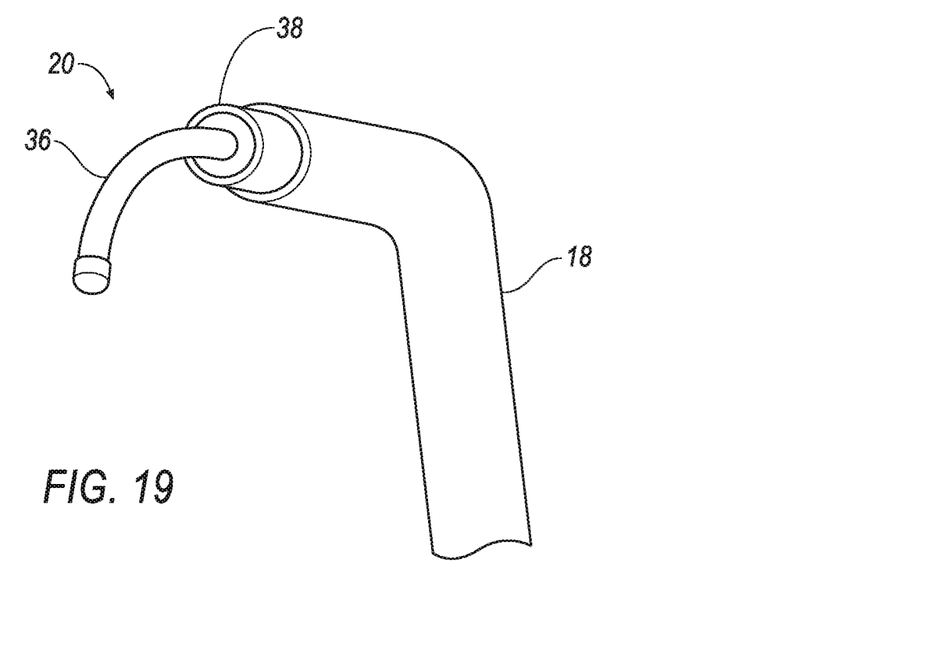
FIG. 19 is a perspective view of an electrosurgical electrode according to an aspect of the invention.

Referring now to FIG. 19, another aspect of the invention is shown and described. In FIG. 19, tubular housing 18 is shown having a curved configuration. Electrode 36, similar to some of the aforementioned embodiments, also has a curved configuration. Curvature of tubular housing 18 curving electrode 36 as the electrodes 36 exits distal end 20 of tubular housing 18.

Figure 20:
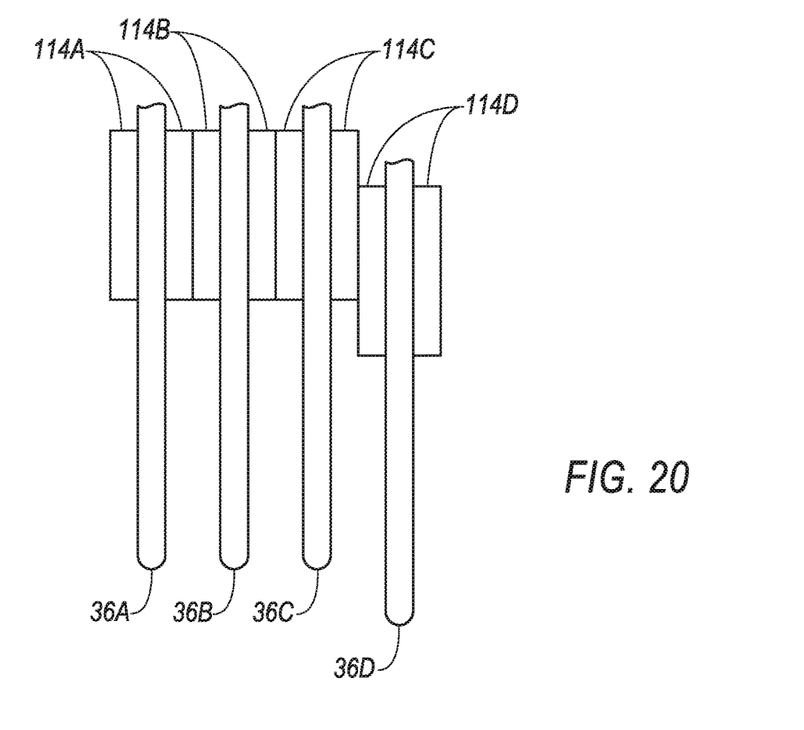
FIG. 20 is a schematic view of an electrosurgical electrode according to an aspect of the invention.

Referring now to FIG. 20, an embodiment of the actuation of electrodes 36 is shown and described. In FIG. 20, a plurality of electrodes 36A through 36D are shown positioned adjacent to one another. Each of the electrodes 36A through 36D are mounted in FIGS. 1 through 4 respectively. It will be understood that triggers 36A and 36D may be any triggering device that permits a user of the electrosurgical device 10 to cause any of the electrodes to exit tubular housing 18. For example, triggers 36A through 36D may be independent triggering devices and mounted similar to that shown for front body part 14 and rear body part 16. Accordingly, in the present embodiment, when a user or surgeon desires to initiate movement of only one electrode, for example only electrode 36A in FIG. 6, then only one of the triggers 114 would be triggered. Thus in the present example, trigger 114D could be initiated to move electrode 36D out of distal end 20 while the remainder of electrodes 36A through 36C remain retracted.

Figure 21:
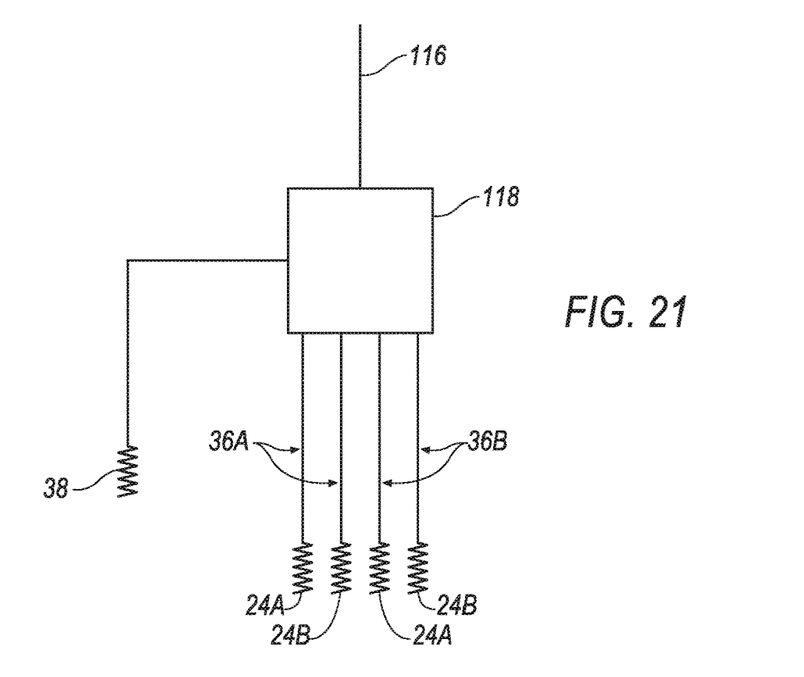
FIG. 21 is a diagrammatic view of an electrosurgical instrument according to an aspect of the invention.

Referring now to FIG. 21, the circuit diagram depicting a circuit according to an embodiment of the present invention is shown and described. In FIG. 21, IC circuit 118 is shown electrically connected to input 116, conductive sheath 38, electrode 36A and corresponding tip portions 24A and 24B, and electrode 36B and corresponding tip portions 24A and 24B. IC circuit 118 provides a number of outputs to each of the respective components depending on desired characteristics requested by a surgeon. It will also be understood that additional electrodes as described in any of the aforementioned embodiments may also be connected to IC circuit 118. To provide desired outputs. In one aspect, IC circuit 118 activates electrode 36A such that tip portion 24A is positive and tip portion 24B is negative. In another aspect, IC circuit 118 grounds conductive sheath 38 such that conductive sheath 38 is negative. In another aspect, IC circuit 118 activates electrode 36B such that tip portion 24A and tip portion 24B are positive and negative respectively. In another aspect, IC circuit 118 activates only tip portion 24A of the electrodes 36A to be positive while grounding conductive sheath 38 to create a monopolar relationship. In a further aspect, IC circuit 118 distributes charge to each of the respective electrodes 36A and 36B in accordance with the previously discussed charging characteristics at a particular frequency. For example, IC circuit 118 may activate electrode 36A while keeping electrode 36B deactivated and then, subsequently, activating electrode 36B and deactivate electrode 36A. This cycle may be repeated any particular frequency set by the surgeon through IC circuit 118. This frequency approach may also be employed with respect to any of the electrodes and the conductive sheath 38.

Figure 22:
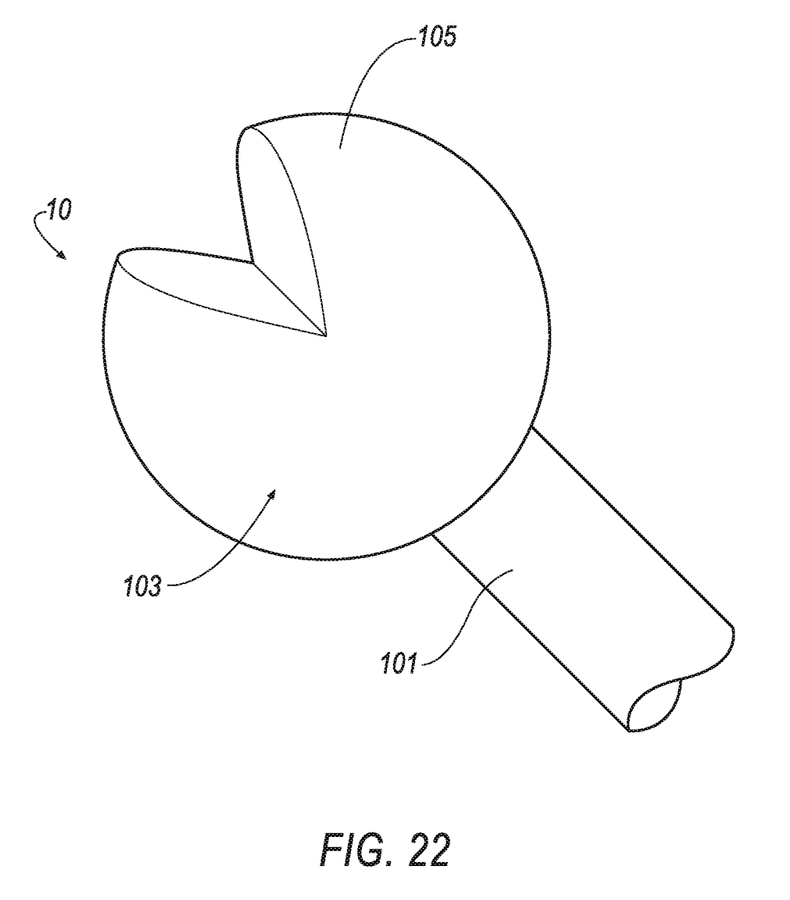
FIG. 22 is a schematic view of an electrosurgical electrode according to an aspect of the invention

Referring now to FIG. 22, another embodiment is shown and described. In FIG. 22, an electrode is shown that could be used instead of any of the previously described electrodes. Here, the electrode is shown having a body 103 having a first half 105 and a second half 107. The first half and second half may be monopolar such that they have the same polarity (positive for example) and ground or conduct through a patient body or through a grounding sheath. Alternatively, a bipolar arrangement may be used where first half is positive while second half is negative with a dielectric region located in body 103 that insulates first half 105 from second half 107.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An electrosurgical device for conducting surgery, said device comprising:
   a tubular housing;
   a plurality of electrodes disposed within said tubular housing;
   an actuator connected to said plurality of electrodes to extend and retract at least one of said plurality electrodes to and from the tubular housing independent of a remainder of the plurality of electrodes;
   wherein each of the plurality of electrodes has at least two conductors separated by a dielectric region to form a bipolar electrode;
   wherein each of the electrodes includes a semispherical head portion; and
   wherein at least one of the head portions is separated into quarter spheres by a dielectric region to electrically isolate said quarter spheres, wherein the at least one of the head portions is a head portion of a bipolar electrode.

2. The electrosurgical device according to claim 1, further comprising:
   a conductive sheath connected to a ground and disposed around the plurality of electrodes;
   wherein the conductive sheath is positioned between the plurality of electrodes and the tubular housing;
   wherein the conductive sheath completes an electrical circuit with the plurality of electrodes.

3. The electrosurgical device according to claim 1, wherein the tubular housing includes an angular bend that angles the plurality of electrodes from a longitudinal axis of the electrosurgical device.

4. The electrosurgical device according to claim 1, wherein each of the plurality of electrodes has a predefined curvature, wherein each of the plurality of electrodes curves with respect to a face of the tubular housing when exiting the face of the tubular housing.

5. The electrosurgical device according to claim 1, wherein a number of the plurality of electrodes is four.

6. The electrosurgical device according to claim 1, wherein at least one of the plurality of electrodes has a predefined curvature, wherein each of the plurality of electrodes curves with respect to a face of the tubular housing when exiting the face of the tubular housing.

7. The electrosurgical device according to claim 6, wherein the tubular housing has a predefined curve; the predefined curve of the tubular housing curves in a same direction as the predefined curvature of the at least one of the plurality of electrodes.

8. The electrosurgical device according to claim 6, wherein the predefined curve of the tubular housing curves in an opposite direction as the predefined curvature of the at least one of the plurality of electrodes.

9. The electrosurgical device according to claim 1, wherein the at least one electrode is two electrodes.

* * * * *